United States Patent [19]

Kert

[11] Patent Number: 5,588,835
[45] Date of Patent: Dec. 31, 1996

[54] ENDODONTIC OBTURATOR

[76] Inventor: Jimmie Kert, Norrevanget 76, DK-3500 Vaerlose, Denmark

[21] Appl. No.: 551,698

[22] Filed: Nov. 1, 1995

Related U.S. Application Data

[63] Continuation of Ser. No. 325,664, Oct. 19, 1994, abandoned.

[51] Int. Cl.$^6$ .............................. A61G 5/02; A61C 5/02
[52] U.S. Cl. .............................................. 433/81; 433/102
[58] Field of Search .............................. 433/81, 102, 224

[56] References Cited

U.S. PATENT DOCUMENTS

| | | | |
|---|---|---|---|
| 5,051,093 | 9/1991 | Fitzmorris | 433/224 |
| 5,275,562 | 1/1994 | McSpadden | 433/224 |

FOREIGN PATENT DOCUMENTS

| | | | |
|---|---|---|---|
| 3112825 | 10/1982 | Germany | 433/81 |

*Primary Examiner*—Nicholas D. Lucchesi
*Attorney, Agent, or Firm*—Larson And Taylor

[57] ABSTRACT

In an appliance for use in filling an endodontically prepared root canal of the kind comprising
a) a central insertion rod (2) of flexible material, surrounded partly by
b) an elongate filler body (3) of plastic or thermoplastic material, the new feature is represented by
c) a core (4) surrounding the rod (2) and surrounded by the filler body (3) and consisting of material that is or may be made sufficiently soft to allow removal of the rod (2) without removal of the filler body (3).

One advantageous effect of this arrangement is that anchoring holes for a tooth crown may be drilled without risk of encountering a broken-off part of an insertion rod that would previously have been left to remain permanently in the filler body (3).

6 Claims, 1 Drawing Sheet

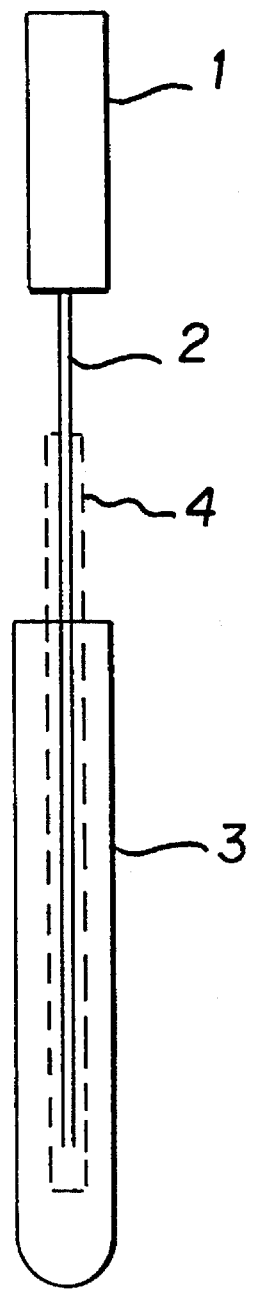

ENDODONTIC OBTURATOR

This application is a continuation of application Ser. No. 08/325,664 filed Oct. 19, 1994, now abandoned.

TECHNICAL FIELD

The present invention relates to an appliance for use in filling an endodontically prepared root canal and of the kind comprising a) a central insertion rod of flexible material, surrounded partly by b) an elongate filler body of plastic or thermoplastic material.

BACKGROUND ART

In appliances of this kind, disclosed i.a. by William B. Johnson in U.S. Pat. No. 4,758,156, the central insertion rod is adapted to be severed when the filler body has been placed in its final position in the root canal. This means, of course, that a part of the insertion rod remains permanently in the root canal. In many cases, this does not cause any problems, but—as will be well-known by dentists—teeth having been treated by the use of such an appliance are also frequently in need of a crown.

As likewise well-known by dentists, tooth crowns have to be anchored to the tooth concerned in a reliable manner, this normally requiring the drilling of at least one suitable anchoring hole. Such drilling is, however, made difficult by the part of the insertion rod remaining in the root canal. Thus, if the insertion rod was made of metal, such as titanium, drilling is almost impossible, while if the insertion rod was made of a hard thermoplastic material, the drilling operation may cause it to melt and clog the drill.

DISCLOSURE OF THE INVENTION

It is the object of the present invention to provide an appliance of the kind referred to initially, with which it is possible to avoid the problems described above, and this object is achieved with such an appliance, according to the invention being characterized by a core surrounding said rod and surrounded by said filler body and consisting of material that is or may be made sufficiently soft to allow removal of said rod without removal of said filler body. With this arrangement, it is no longer necessary to leave a part of the insertion rod remaining permanently in the root canal and causing the problems described above.

According to a first embodiment of the invention, the rod may be made of carbon steel. This is a comparatively inexpensive material having excellent qualities with regard to elasticity and strength requisite for the use for which it is intended.

According to a second embodiment, the core consists of a material capable of being softened by heat. With this embodiment, the insertion rod may be removed easily after having been heated on the part extending outside of the core and the filler body.

According to a third embodiment, the insertion rod may be helically wound or twisted or formed with a steep thread so as to make it possible to unscrew it from the core, thus facilitating the removal of the insertion rod from the filler body and the core.

According to a fourth embodiment, the core may consist of or comprise material that is opaque to tissue-penetrating rays. With this embodiment, it is possible to locate the root canal by using x-rays, the core now in this respect playing the same role as previously played by a part of a metal insertion rod remaining in the root canal.

BRIEF DESCRIPTION OF THE DRAWINGS

In the following detailed portion of the present description, the invention will be explained in more detail with reference to the exemplary embodiment of an appliance according to the invention diagramatically shown in the single figure.

DESCRIPTION OF THE PREFERRED EMBODIMENT

The endodontic obturator shown in the drawing comprises:

a handle 1, made e.g. from some suitable plastic material, an insertion rod 2, made e.g. from carbon steel, and a filler body 3 of gutta-percha surrounding the lowermost part of the insertion rod 2.

The three parts 1–3 described in the previous paragraph may be said to belong to the prior art. The novel feature of the invention is represented by a core 4 surrounding the insertion rod 2 and itself being surrounded by the filler body 3. The core 4 is made of a material that is sufficiently soft, or can be made sufficiently soft, so as to make it possible to remove the insertion rod 2 from the filler body 3, when the latter has been placed in its final position in a root canal of a tooth (not shown). Persons with knowledge of plastic materials will know how to choose the correct material for the core 4 according to requirements. In practice, the appliance is used in the following manner.

When the root canal has been prepared, the appliance is inserted in the canal with the filler body 3 leading, possibly after suitable pre-heating of the filler body to make it sufficiently soft to adapt itself to the walls of the root canal. During the insertion, the device is held and moved by means of the handle 1.

When the filler body 3 has been placed in its final position in the root canal, and sufficient time has elapsed to allow it to cure or set (if necessary), the insertion rod 2 is removed by means of the handle 1. If the surface of the insertion rod 2 is smooth, it may be removed by simply pulling the handle 1, but if it is helically wound or twisted or formed with a steep thread, it may be unscrewed by turning the handle 1 in the appropriate direction.

If the core 4 is made of a thermoplastic material that is relatively stiff at the temperatures encountered, the removal of the handle 1 may be facilitated by gently heating the part of the insertion rod 2 not being covered with core material.

When the insertion rod 2 has been removed, any excess core material may be removed, after which the root canal is closed and provided with a top filling in the normal manner. At this stage only the filler body 3 and the core 4 remain in the part of the root canal, into which they were inserted. It is now possible to drill an anchoring hole into or intersecting the root canal without the risk of the drill encountering materials causing problems of the kind referred to initially.

Obviously, both the filler body 3 and the core 4 will have to be made of suitable tissue-friendly materials.

The dimensions of the insertion rod 2, the filler body 3 and the core 4 may be varied according to need.

I claim:

1. Appliance for use in filling an endodontically prepared root canal and of the kind comprising:

a) a central insertion rod (2) surrounded partly by b) an elongate filler body (3, 4) of plastic material consisting of a core (4) and an outer filler body (3), said core (4) surrounding said rod (2) and said outer filler body (3) surrounding said core (4), said core (4) and said outer filler body (3) consisting of materials of differing softening points, and c) the softening point of the material of said core (4) being lower than that of the material of said outer filler body (3).

2. Appliance according to claim 1, wherein said rod (2) is made of flexible carbon-steel material.

3. Appliance according to claim 1 or 2, wherein said rod (2) is twisted thread so as to enable it to be unscrewed from said core (4).

4. Appliance according to claim 1 wherein said core (4) comprises material that is opaque to x-rays.

5. Appliance according to claim 1 wherein the rod (2) is helically wound so as to enable it to be unscrewed from said core (4).

6. Appliance for use in filling an endodontically prepared root canal and of the kind comprising:

a) a central insertion rod (2) surrounded partly by b) an elongate filler body (3, 4) of plastic material consisting of a core (4) and an outer filler body (3), said core (4) surrounding said rod (2) and said outer filler body (3) surrounding said core (4), said core (4) and said outer filler body (3) consisting of materials of differing melting points, and c) the melting point of the material of said core (4) being lower than that of the material of said outer filler body (3).

* * * * *